United States Patent [19]

Schumacher

[11] Patent Number: 4,757,043
[45] Date of Patent: Jul. 12, 1988

[54] PROCESS FOR PREPARING VAPOR PHASE NITRATION CATALYSTS

[75] Inventor: Ignatius Schumacher, Ballwin, Mo.

[73] Assignee: Monsanto Company, St. Louis, Mo.

[21] Appl. No.: 671,358

[22] Filed: Nov. 14, 1984

[51] Int. Cl.[4] .................... B01J 27/24; B01J 27/02; B01J 23/00

[52] U.S. Cl. .................... 502/200; 502/216; 502/302; 502/303; 502/349; 502/351

[58] Field of Search .............. 502/200, 216, 303, 351, 502/349, 302

[56] References Cited

U.S. PATENT DOCUMENTS

| | | | |
|---|---|---|---|
| 2,109,873 | 3/1938 | Wilhelm | 568/939 |
| 3,159,569 | 12/1964 | Hansford | 502/216 X |
| 3,180,900 | 4/1965 | Sparks | 568/937 |
| 3,873,674 | 3/1975 | Rosenthal et al. | 423/538 X |
| 3,928,476 | 12/1975 | Shinada et al. | 502/208 X |
| 3,929,670 | 12/1975 | Kudo et al. | 502/244 |
| 3,978,200 | 8/1976 | Bajars | 423/564 |
| 4,002,720 | 1/1977 | Wheelock et al. | 423/244 A X |
| 4,064,171 | 12/1977 | Weigert | 260/581 |
| 4,107,220 | 8/1978 | Owsley et al. | 568/937 |
| 4,117,099 | 9/1978 | Merkl | 502/216 X |
| 4,151,123 | 4/1979 | McCann | 423/213.2 X |
| 4,243,825 | 1/1981 | Williamson et al. | 585/428 |
| 4,254,293 | 3/1981 | Tremont et al. | 585/422 X |
| 4,328,373 | 5/1982 | Strojny | 568/435 |
| 4,347,389 | 8/1982 | Schumacher et al. | 568/937 |
| 4,350,613 | 9/1982 | Nishino et al. | 502/200 |
| 4,415,744 | 11/1983 | Schumacher et al. | 502/240 X |
| 4,451,342 | 5/1984 | Lichtin et al. | 204/157.1 R |

FOREIGN PATENT DOCUMENTS

| | | | |
|---|---|---|---|
| 53-63267 | 6/1978 | Japan | 502/303 |
| 54-167044 | 12/1984 | Japan | 502/303 |

Primary Examiner—Helen M. S. Sneed
Assistant Examiner—William G. Wright
Attorney, Agent, or Firm—Wendell W. Brooks; Arthur E. Hoffman; Arnold H. Cole

[57] ABSTRACT

Catalysts useful to catalyze the nitration of aromatic compounds in the vapor phase to produce nitroaromatic compounds are prepared by contacting a Group 4b-Group 3b metal oxide composition represented by the empirical formula:

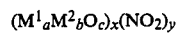

$$(M^1{}_a M^2{}_b O_c)_x (NO_2)_y$$

wherein $M^1$ is at least one element selected from Group 4b of the Periodic Table of the Elements, $M^2$ is at least one element selected from Group 3b of the Periodic Table of the Elements, a is 1, b is 0 to 20, c is a number taken to satisfy the average valences of $M^1$ and $M^2$ in the oxidation states in which they exist in the composition, x is 1, and y is 0 to c, with a catalytically effective amount of sulfur trioxide. Such catalysts are particularly effective to catalyze the vapor phase nitration of chlorobenzene and are characterized in such reaction by providing a para/ortho isomer distribution ratio of at least about 2/1.

12 Claims, No Drawings

PROCESS FOR PREPARING VAPOR PHASE NITRATION CATALYSTS

BACKGROUND OF THE INVENTION

1. Field of the Invention

This invention relates to a process for the preparation of vapor phase nitration catalysts. More particularly, this invention relates to a process for the preparation of nitration promoting catalysts useful to catalyze the nitration of aromatic compounds in the vapor phase to produce nitroaromatic compounds which comprises contacting a Group 4b-Group 3b mixed oxide composition represented by vthe empirical formula:

$$(M^1{}_aM^2{}_bO_c)_x(NO_2)_y$$

wherein $M^1$ is at least one element selected from Group 4b of the Periodic Table of the Elements, $M^2$ is at least one element selected from Group 3b of the Periodic Table of the Elements, a is 1, b is 0 to 20, c is a number taken to satisfy the average valences of $M^1$ and $M^2$ in the oxidation states in which they exist in the composition, x is 1, and y is 0 to c, with a catalytically effective amount of sulfur trioxide. The catalysts are characterized by exhibiting a para/ortho isomer distribution of at least about 2/1 during the nitration of monosubstituted aromatic compounds having an ortho-para orientation substituent, especially chlorobenzene.

Nitroaromatic compounds find use as solvents, explosives, dyes, perfumes, and analytical reagents, and are important as intermediates in organic synthesis. As an example, nitroaromatic compounds are convertible by reduction into primary amines, which in turn, are valuable intermediates in the synthesis of dyes, pharmaceuticals, photographic developers, antioxidants, and gum inhibitors.

2. Description of the Prior Art

Nitroaromatic compounds are currently produced primarily via liquid phase reactions employing mixed acids. A sulfuric acid/nitric acid mixture is the most commonly employed industrial nitrating agent. Other mixed acids for nitration of aromatic compounds are acetic acid/nitric acid mixtures as described, for example, in U.S. Pat. No. 3,180,900. In U.S. Pat. No. 3,928,476, the latter type nitration is conducted over silica-alumina or alumina supports.

Vapor phase nitration of aromatic compounds is also known in the art. The vapor phase nitration of benzene and toluene at temperatures ranging from about 275° to about 310° C. is described in McKee and Wilhelm, *Industrial and Engineering Chemistry*, 28 (6), 662–667 (1936) and U.S. Pat. No. 2,109,873. McKee and Wilhelm catalyze their reaction with silica gel, with best results being reported by the use of 14 mesh material. Bauxite and alumina were reported to be ineffective as catalysts in the vapor phase nitration of benzene.

In U.S. Pat. No. 4,107,220, the vapor phase nitration of chlorobenzene in the presence of molecular sieve catalysts having a pore size varying from about 5 Å to about 10 Å as a means for controlling the para-to-ortho isomer distribution of nitrochlorobenzene is described. A suitable temperature range was reported to be from about 190° C. to about 290° C.

U.S. Pat. No. 4,347,389 describes a process for the vapor phase nitration of aromatic compounds. The process comprises contacting the aromatic compound with a nitrating agent in the presence of nitration promoting catalyst comprising a phosphorus-vanadium-oxygen complex.

More recently, in U.S. Pat. No. 4,415,744, a process is described for the vapor phase nitration of aromatic compounds in the presence of a specific catalyst composition. In this process, aromatic compounds are contacted in the vapor phase with a nitrating agent in the presence of a nitration promoting catalyst which comprises the adduct of:

(a) an alumina-silica-metal oxide combination represented by the formula:

$$(Al_2O_3)_a(SiO_2)_b(M_{2/n}O)_c$$

wherein M is a metal cation selected from the group consisting of the lanthanides or rare earths, Groups 1b, 2b, 5b, 6b, 7b, and 8 of the Periodic Table of the Elements, and mixtures thereof, and a, b, and c represent weight percent of the $Al_2O_3$, $SiO_2$ and $M_{2/n}O$ components, respectively, in the alumina-silica-metal oxide combination, with a being 0 to 100, b being 0 to 100, and c being 0 to 50, and n represents an integer from 1 to 7 of the valence of the metal cation, with the proviso that the sum of (a+b) must be greater than 0, and (b) a catalytically effective amount of sulfur trioxide.

Although catalysts prepared by processes of the prior art are effective to provide the nitrated aromatic compounds, the choice of available catalysts is severely limited. In addition, the commercial utility of a catalyst system is highly dependent upon the cost of the system, the conversion of the reactant(s) and the selectivity and yield of the desired product(s). In many cases, a reduction in the cost of a catalyst system on the order of a few cents per kilogram or pound or a small increase in the yield of the desired product represents a tremendous commercial economical savings. Accordingly, research efforts are continually being made to define new or improved catalyst systems and methods and processes of making new and old catalyst systems to reduce the cost and/or upgrade the activity and selectivity of such catalyst systems in particular processes. The discovery of the process of the present invention, therefore, is believed to be a decided advance in the catalyst art.

SUMMARY OF THE INVENTION

It is an object of this invention to provide a process for preparing novel nitration promoting catalysts highly effective for the vapor phase nitration of aromatic compounds.

Another object of this invention is to provide a process for preparing novel nitration promoting catalysts highly effective in controlling the para/ortho isomer distribution to at least about 2/1 during the vapor phase nitration of monosubstituted aromatic compounds having an ortho/para orientation substituent, especially chlorobenzene.

To achieve these and other objects which will become apparent from the accompanying description and claims, a process is provided for preparing nitration promoting catalysts which comprises contacting a Group 4b-Group 3b mixed oxide composition represented by the empirical formula:

$$(M^1{}_aM^2{}_bO_c)_x(NO_2)_y$$

wherein $M^1$ is at least one element selected from Group 4b of the Periodic Table of the Elements, $M^2$ is at least one element selected from Group 3b of the Periodic Table of the Elements, a is 1, b is 0 to 20, c is a number taken to satisfy the average valences of $M^1$ and $M^2$ is the oxidation states in which they exist in the composition, x is 1, and y is 0 to c, with a catalytically effective amount of sulfur trioxide.

DESCRIPTION OF THE PREFERRED EMBODIMENTS

In accordance with this invention, a process is provided for the preparation of novel nitration promoting catalysts which are useful to catalyze the nitration of aromatic compounds in the vapor phase to produce nitroaromatic compounds. These nitration promoting catalysts are prepared by a process which comprises contacting a Group 4b-Group 3b mixed oxide composition represented by the empirical formula:

$$(M^1_a M^2_b O_c)_x (NO_2)_y$$

wherein $M^1$ is at least one element selected from Group 4b of the Periodic Table of the Elements, $M^2$ is at least one element selected from Group 3b of the Periodic Table of the Elements, a is 1, b is 0 to 20, c is a number taken to satisfy the average valences of $M^1$ and $M^2$ in the oxidation states in which they exist in the composition, x is 1, and y is 0 to c, with a catalytically effective amount of sulfur trioxide.

Group 4b-Group 3b mixed oxide composition materials suitable for use in the instant invention are those which yield the unique nitration promoting catalysts prepared in accordance with the instant invention. Such catalysts are sufficiently active to catalyze the desired vapor phase nitration of aromatic compounds, while at the same time sufficiently selective to control the para-/ortho isomer distribution to at least about 2/1 and up to about 4/1 and higher during the vapor phase nitration of monosubstituted aromatic compounds having an ortho-para orientation substituent, for example, chlorobenzene. Moreover, the high selectivity exhibited by such catalysts, in contrast to prior art catalysts, also advantageously results in the substantial absence of the production of contaminating by-products such as di- and polynitroaromatic compounds during the vapor phase nitration reaction.

Compounds useful as a source of the necessary Group 4b element ($M^1$) include Group 4b oxides and salts and hydroxides which are convertible by heat into the corresponding oxide. As such, the latter compounds which can be used to provide indirectly the Group 4b oxide may be considered as precursors of the oxides, Typical salts include the nitrates, carbonates, and acetates. Such compounds are available commercially from numerous catalyst and metal suppliers.

Of these compounds, the oxides, hydroxides, and nitrates of Group 4b are generally preferred, with such compounds of titanium and zirconium and mixtures thereof being most preferred. It will be noted, of course, that titanium and zirconium are the Group 4b elements of choice in any event. That is, regardless of whether the initial form of the Group 4b compound employed is an oxide, hydroxide, or salt such as the nitrate, titanium and zirconium are the preferred Group 4b elements.

Group 3b compounds suitable as a source for the Group 3b element ($M^2$), in a manner similar to that described for the Group 4b compounds, include the oxides, hydroxides, and salts of Group 3b, the latter two groups being convertible by heat into the corresponding oxide. Suitable Group 3b oxides are exemplified by scandium oxide ($Sc_2O_3$), yttrium oxide ($Y_2O_3$), lanthanum oxide ($La_2O_3$), actinium oxide ($Ac_2O_3$), and the oxides of the lanthanides and actinides, and mixtures thereof. Typical Group 3b salts include the nitrates, carbonates, and acetates.

Of the Group 3b compounds, the compounds of lanthanum are the compounds of choice, with the oxides, hydroxides, and nitrates being generally preferred. As a practical matter, the nitrates are generally most preferred in that they are readily available, are soluble in a number of solvents which aid in the Group 4b-Group 3b mixed oxide composition preparation. In addition, any residual nitro groups, or moieties remaining in the Group 4b-Group 3b mixed oxide composition causes no adverse effect upon the formation of the nitration promoting catalyst and the subsequent nitration reaction since such groups in the presence of the nitrating agent then become common to the reaction environment.

The term "Periodic Table of the Elements", as employed herein, refers to the Periodic Table of the Elements published in *CRC Handbook of Chemistry and Physics*, 65th ed., Weast, Ed., CRC Press, Inc., Boca Raton, FL, 1984, Inside Front Cover.

The Group 4b-Group 3b mixed oxide compositions suitable for use in the process of the instant invention can be prepared by any one of a wide variety of procedures or methods. One such method involves intimately mixing the powdered Group 3b and Group 4b oxides in the dry state and calcining. Another method involves slurrying the Group 3b and Group 4b oxides in a suitable liquid medium, for example, water or an organic compound such as methanol, ethanol, acetone, and the like, filtering to remove excess liquid or, alternatively, heating to evaporate the liquid, drying, and calcining. In another method of preparation, the powdered Group 3b and Group 4b oxides can be intimately mixed before forming a paste of them with water and further mixing the paste. The paste can be spread and dried in air or in an inert atmosphere, for example, nitrogen, after which it can be calcined in air or an inert atmosphere. The calcined product can then be crushed and sieved to the desired mesh size. In still another method of preparation, the powdered Group 3b and Group 4b oxides can be mixed in the dry state together with a material which facilitates forming the mixture into pellets and then pressed to form pellets which are calcined prior to use. A further method of preparation involves intimately mixing the powdered Group 3b and Group 4b oxides in water and spray drying the resulting slurry or solution to produce relatively dust-free and free-flowing spherical particles which are also calcined prior to use.

In another method of preparation, Group 3b and Group 4b oxide precursor salts such as nitrates, carbonates, and acetates are intimately mixed or dissolved in a suitable liquid medium, for example, water, nitric acid, or a previously noted suitable organic compound, and heated to thermally decompose the precursor salts to form the corresponding oxides. The oxides can then be treated as described hereinabove prior to use.

In still another method of preparation, at least one Group 3b oxide precursor salt such as a nitrate, carbonate, and acetate, preferably a nitrate, is dissolved or slurried in a suitable liquid medium, as previously noted, and intimately mixed with a Group 4b oxide. The liquid can be removed by gentle heating under reduced pressure, which pressure, for convenience, will in general range from about $6.67 \times 10^4$ Pa-G (500 mm Hg) to about $8.67 \times 10^4$ Pa-G (650 mm Hg) or less. The resulting material is calcined prior to use.

Yet another method of preparation involves slurrying a Group 3b oxide precursor salt with a Group 4b oxide in a liquid medium until a uniform mix is obtained. The liquid can be removed by evaporation as previously described. The resulting solid material is ground to a suitable mesh size, typically less than 60 mesh (U.S. Standard Sieve Size) and intimately mixed with a pelletizing agent, for example, powdered graphite, and pressed into pellets which are calcined prior to use.

The calcination may be carried out in air or an inert atmosphere such as nitrogen, helium, argon, and the like, at subatmospheric, atmospheric, or superatmospheric pressures. As a practical matter, however, atmospheric pressures are generally preferred.

Temperatures suitable for calcination of the Group 4b-Group 3b mixed oxide compositions may vary from about 125° C. to about 400° C., although higher temperatures up to about 1200° C. may be employed, if desired. Preferred calcination temperatures generally lie in the range from about 140° C. to about 200° C. Calcination times may vary from about 1 hour to about 12 hours or more, and preferably from about 2 hours to about 10 hours.

Sulfur trioxide ($SO_3$) is an essential component of the nitration promoting catalysts prepared in accordance with the process of the instant invention. It is added to the Group 4b-Group 3b mixed oxide composition in a catalytically effective amount. It may be charged directly as sulfur trioxide in the vapor or gaseous phase. Alternatively, it may be provided indirectly by charging to the Group 4b-Group 3b mixed oxide composition a mixture of sulfur dioxide ($SO_2$) and nitrogen dioxide ($NO_2$) which react to produce sulfur trioxide and inert (for purposes of the instant invention) nitric oxide (NO). When a mixture of sulfur dioxide and nitrogen dioxide is employed, a stoichiometric mole ratio of at least one (1) is required. It is preferred, however, to employ an excess of sulfur dioxide, usually on the order of about 2 to 3 moles per mole of nitrogen dioxide.

In general, when providing the sulfur trioxide, the indirect method of charging a mixture of sulfur dioxide and nitrogen dioxide to the Group 4b-Group 3b mixed oxide composition is preferred in that both sulfur dioxide and nitrogen dioxide, as well as nitric oxide, exist in the gaseous state at ambient temperatures (approximately 25° C.) and above while sulfur trioxide exists as a liquid at ambient temperatures and under the usual and preferred preparative conditions would first have to be converted to a vapor prior to contacting the Group 4b-Group 3b mixed oxide composition.

As previously indicated, the nitration promoting catalysts prepared in accordance with the process of the instant invention comprise an adduct, an essential component of which is sulfur trioxide. It is recognized, of course, that when a mixture of sulfur dioxide and nitrogen dioxide is charged to the reactor to provide the sulfur trioxide, the absorbed species may in fact be a complex or combination of sulfur trioxide and nitrogen dioxide. However, regardless of the actual composition of the adsorbed species, it is conveniently referred to herein as sulfur trioxide and is meant to encompass all such compositions, whether sulfur trioxide, sulfur trioxide-nitrogen dioxide complex, or some combination thereof, as well as unreacted mixtures of sulfur dioxide and nitrogen dioxide.

The nitration promoting catalysts prepared in accordance with the process of the instant invention are normally prepared by contacting the Group 4b-Group 3b mixed oxide composition with sulfur trioxide (directly or indirectly as previously described) in the vapor phase under conditions conducive to the formation of the adduct and for a time sufficient to induce the desired weight gain. The amount of added sulfur trioxide (as indicated by the gain in weight) is not narrowly critical. All that is necessary is that a catalytically effective amount of sulfur trioxide be added. In general, it has been found that at least one (1) weight percent, based on the weight of the Group 4b-Group 3b mixed oxide composition, sulfur trioxide is required to provide the enhanced activity exhibited by the catalysts of the instant invention. Also, although not critical, an upper limit of about 40 weight percent, with about 3 weight percent to about 10 weight percent being preferred, has been found to be desirable in that little, if any, advantage is demonstrated for higher concentrations of sulfur trioxide. Thus, both higher and even lower concentrations then the stated one (1) to 40 weight percent range can be employed, if desired, but since such concentrations offer no particular advantage over the stated desirable range, and may in fact affect adversely the catalyst activity, particularly at concentrations less than about one (1) weight percent, the stated one (1) to 40 weight percent range is desirably employed, with about 3 to about 10 weight percent being preferred.

The conditions under which the nitration promoting catalysts are prepared can vary widely. All that is necessary is that the sulfur trioxide, whether charged directly or indirectly, exist in the vapor phase while contacting the Group 4b-Group 3b mixed oxide composition. Thus, the catalyst preparation can be conducted at temperatures ranging from ambient temperatures (about 25° C.) (when sulfur dioxide and nitrogen dioxide are employed to provide the sulfur trioxide) to about 300° C. or higher. Preferred temperatures, however, range from about 150° C. to about 250° C., with 175° C. to about 225° C. being particularly preferred. At such preferred temperatures, the uptake of sulfur trioxide is reasonably rapid with a minimum of loss of reactant gases resulting from unreacted pass-through. In general, and for convenience, the catalyst preparations can be performed at the temperature to be employed in the subsequent reaction in which the catalyst is to be employed.

In nitration promoting catalyst preparations are conducted under substantially anhydrous conditions. This is necessary since sulfur trioxide readily undergoes reaction with water to form sulfuric acid which, prior to formation of the adducts comprising the catalyst compositions of the instant invention, may exhibit an adverse effect in subsequent reactions. As employed herein, the term "substantially anhydrous" means not more than 5 weight percent water is present in the reaction as part of the nitration promoting catalyst-forming components.

The nitration promoting catalysts prepared in accordance with the process of the instant invention are conveniently prepared in an apparatus of the type suitable for carrying out chemical reaction in the vapor phase. In this manner the catalyst preparation can be performed in the same reactor as that to be employed for the subsequent vapor phase nitration reaction. In a manner similar to that discussed hereinbelow for carrying out vapor phase nitration reactions using the nitration promoting catalysts prepared in accordance with the process of the instant invention, the catalyst preparation can be conducted in a fixed bed, moving bed, or a fluidized bed system to effect contacting of the Group 4b-Group 3b mixed oxide composition and the sulfur trioxide. And, a previously noted, catalyst preparation preferably is carried out by continually passing a vaporous mixture of sulfur dioxide and nitrogen dioxide in a 2-3/1 mole ratio over a bed of the Group 4b-Group 3b mixed oxide composition under substantially anhydrous conditions at a temperature from about 25° C. to about 300° C., and usually, about 175° C. to about 225° C.

The nitration promoting catalysts prepared in accordance with the process of the instant invention are useful in a variety of reactors of the type suitable for carrying out reactions in the vapor phase to nitrate aromatic compounds in the vapor phase to yield nitroaromatic compounds. The nitration promoting catalysts may be used in a single reactor or in multiple reactors using a fixed bed, moving bed, or a fluidized bed system to effect contact of the reactants and the nitration promoting catalyst composition. For use in either the fixed bed or moving bed system, the nitration promoting catalysts are conveniently employed as tablets, pellets, or the like. A fluidized bed system, on the other hand, requires the nitration promoting catalysts to be in a finely divided state, preferably having a particle size of less than about 300 microns. Details of the operation of such reactors are well known to those skilled in the art.

The nitration promoting catalysts prepared in accordance with the instant process are particularly useful in fixed bed (tube), heat exchanger type reactors. The tubes of such reactors can vary in diameter from about 0.635 cm (0.25-inch) to about 5.08 cm (2-inches) and the length can vary from about 15.24 cm (6-inches) to about 304.8 cm (10 feet) or more. It is desirable to have the surfaces of the reactors at relatively constant temperatures, and some medium to conduct heat from the reactors is necessary to aid temperature control. Nonlimiting examples of such media include Woods metal, molten sulfur, mercury, molten lead, and eutectic salt baths. A metal block reactor whereby the metal surrounding the tube acts as a temperature regulating body can also be used. The reactor or reactors can be constructed of iron, stainless steel, carbon steel, glass, and the like.

The reaction to nitrate aromatic compounds using the nitration promoting catalysts prepared in accordance with the process of the instant invention is carried out by contacting the aromatic compound with a nitrating agent in the vapor phase in the presence of (at least one of) the nitration promoting catalysts prepared in accordance with the instant process. The nitration promoting catalysts are characterized by an observed para/ortho isomer distribution of at least about 2/1 up to about 4/1 and higher when the aromatic compound is a monosubstituted aromatic compound having an ortho-para orientation substituent, especially chlorobenzene. In addition, such catalysts, in contrast to catalysts of the prior art, substantially eliminates the production of contaminating by-products such as di- and polynitroaromatic compounds during the vapor phase nitration reaction.

Aromatic compounds suitable for use in carrying out vapor phase nitration reactions are those which can exist in the vapor phase or state and undergo nitration under operating conditions to yield the desired nitroaromatic compounds. Moreover, in those instances where ortho and/or para isomers of the nitroaromatic compound are desired, the aromatic compound starting material must have an ortho-para orientation substituent such as halogen, lower alkyl, lower hydroxyalkyl, lower acetoxyalkyl, lower alkoxy, phenol, and the like, where the term "lower alkyl" and related terms refer to substituents containing alkyl groups of 1 to 6 carbon atoms. Nonlimiting representatives of suitable aromatic compounds include aromatic hydrocarbons, such as benzene, toluene, xylenes, ethylbenzene, cumene, naphthalene, and the like; aromatic ethers such as anisole, phenetole, and the like; haloaromatic compounds such as chlorobenzene, bromobenzene, iodobenzene, o-dichlorobenzene, and the like; aromatic carboxylates such as benzoic acid, methyl benzoate, ethyl benzoate, and the like. It has been found, however, that the process of this invention is particularly efficacious with chlorobenzene (also known as monochlorobenzene or simply MCB).

It will be apparent, of course, that mono-substituted aromatic compounds having an ortho-para orientation substituent—chlorobenzene, for example—upon being nitrated yield a nitroaromatic compound product containing ortho, meta, and para isomers. In such instances, the ortho and para isomers generally constitute the major portion of the product mixture (para/ortho isomer ratio of at least about 2/1), with the meta isomer being present in only trace amounts.

As nitrating agents, nitric acid and the gaseous oxides of nitrogen higher than nitric oxide (NO) such as nitrogen dioxide ($NO_2$), dinitrogen trioxide ($N_2O_3$), dinitrogen tetroxide ($N_2O_4$), dinitrogen pentoxide ($N_2O_5$), also known as nitric anhydride, and mixtures thereof may be employed. Nitric acid used as a nitrating agent can be of any desired grade. It is advantageous, however, to use commercial grade nitric acid, and nitric acid having a concentration of from about 25 weight percent to about 70 weight percent (concentrated) and a specific gravity of from about 1.2 to about 1.4 is especially preferred.

Nitrogen pentoxide used as a nitrating agent can be obtained, for example, by adding fuming nitric acid to phosphorus pentoxide in a stoichiometric mole ratio of 2 moles of nitric acid per mole of phosphorus pentoxide. It can also be obtained by the oxidation of liquid nitrogen tetroxide with ozone in a 1/1 stoichiometric mole ratio.

Nitrogen dioxide used as a nitrating agent can be obtained by oxidizing nitric oxide, which may be obtained by burning or oxidizing ammonia according to the Ostwald process, or by thermally decomposing nitrogen pentoxide at elevated temperatures in excess of 260° C.

Nitrogen dioxide, of course, exists in equilibrium with its dimer, dinitrogen tetroxide. This equilibrium is strongly temperature dependent. At about room temperature (25° C.), about 80% of the nitrogen dioxide is transformed into the dimeric dinitrogen tetroxide. At 100° C. the equilibrium composition is about 90% nitrogen dioxide and 10% dinitrogen tetroxide. At temperatures in excess of 150° C., dinitrogen tetroxide essentially does not exist. At these conditions, almost all of the dinitrogen tetroxide dissociates into nitrogen dioxide.

Dinitrogen trioxide also dissociates and forms nitrogen dioxide and nitric oxide. It will be noted, however, that since nitric oxide cannot be used as a nitrating agent, the yield per nitrogen atom provided by the dinitrogen trioxide declines.

Of these nitrating agents, nitric acid and nitrogen dioxide are generally preferred. For practical reasons, however, nitric acid is in general most preferred in that it is readily available and relatively inexpensive. In addition, since nitric acid preferred for use as the nitration agent contains approximately 30–75% by weight water, the necessity of separately supplying water to the reaction zone, as discussed hereinbelow, is eliminated.

If desired, the nitration promoting catalyst is conditioned by pretreatment with the nitrating agent at vapor phase nitration conditions (discussed hereinbelow) to the saturation point (in the absence of aromatic compounds). Suitable pretreatment times can range from about 1 minute to about 1 hour or more. The actual pretreatment time, however, will depend upon the amount or quantity and pore structure of the nitration promoting catalyst, the feed rate of the nitrating agent, the operating conditions, and the like. When employed, pretreatment for about 5 minutes to about 15 or 20 minutes is usually sufficient.

The conditioning pretreatment is not a prerequisite for effective vapor phase nitration. In many instances, however, it is desirable because it permits almost immediate production of the nitroaromatic compound upon introduction of the aromatic compound to the reaction zone. In such instances, in the absence of the pretreatment, measurable nitroaromatic compound production may be delayed until the nitration promoting catalyst becomes saturated with the nitrating agent.

The vapor phase nitration reaction is not limited to a specific reaction temperature since the reaction can be conducted at temperatures ranging from about 80° C. to about 300° C. Preferred temperatures, however, range from about 150° C. to about 250° C. with 175° C. to about 225° C. being particularly preferred. At such preferred temperatures, the rate of reaction is reasonably rapid and little, if any, by-product formation occurs. It will be appreciated, however, that the particular temperature employed for a given aromatic compound will depend to some extent upon the boiling point or vaporization temperature of the particular aromatic compound. For example, when chlorobenzene, which has a boiling point of 132° C., is the aromatic compound of choice, the vapor phase nitration is conveniently carried out within the aforesaid preferred and most preferred temperature ranges. When benzene (b.p., 80° C.) is the aromatic compound of choice, the vapor phase nitration may be conducted at temperatures which encompass the entire operative range, that is, from about 80° C. to about 300° C. Again, however, temperatures from about 150° C. to about 250° C. are preferred, with 175° C. to about 225° C. being particularly preferred.

In a similar manner, when a solid compound such as naphthalene or benzoic acid (sublimation temperatures at atmospheric pressure, 80.2° C. and 100° C., respectively) is the aromatic compound of choice, the vapor phase nitration may be conducted at temperatures at or above the vaporization (sublimation) temperature, and preferably within the aforesaid preferred temperature range.

Notwithstanding the stated preferred temperature range, it will be appreciated that higher temperatures may be advantageously employed for more difficult to nitrate aromatic compounds. For example, o-dichlorobenzene (b.p., 179° C.) does not readily undergo nitration within the preferred temperature range of about 150° C. to about 250° C. Thus, in order to effect reasonable conversions and yields, temperatures greater than 250° C. to about 300° C. are preferred.

As previously indicated, the vapor phase nitration reaction can be conducted at temperatures ranging from about 80° C. to about 300° C., with temperatures from about 150° C. to about 250° C. being preferred. Some advantages accruing from conducting the vapor phase nitration reaction at the preferred temperatures include
(a) greater selectivity to the desired nitroaromatic compounds;
(b) little, if any, by-product formation (to contaminate the desired product);
(c) high material balance between reactants and products; and
(d) minimal thermal decomposition of the nitrating agent.

The advantage [(d)] is particularly significant in that it, to a large extent, influences the remaining advantages. It, of course, is well-known in the art that at temperatures in excess of 300° C., the decomposition of nitric acid into what is believed to be initially nitrogen dioxide and water (and molecular oxygen) becomes marked, and the yield of nitration product is reduced. The latter result is believed to be attributable to the well known phenomenon that at elevated temperatures nitrogen dioxide undergoes thermal decomposition into the inert (for purposes of this invention) nitric oxide and molecular oxygen. The decomposition begins at about 150° C. and is complete at about 620° C. The nitrogen dioxide decomposition at various temperatures is as follows:

| Temperature, °C. | 130 | 150 | 184 | 279 | 494 | 620 |
|---|---|---|---|---|---|---|
| Decomposition, % | 0 | 3 | 5 | 13 | 56.5 | 100 |

Thus, at temperatures between about 80° C. and about 300° C. the maximum loss of active nitrogen dioxide by thermal decomposition into inert nitric oxide is only about 15–20%, while at temperatures greater than 300° C., the loss by thermal decomposition rapidly increases to 30% or more, and finally, to 100% at 620° C. In a similar manner, the decomposition of nitric acid is also avoided by carrying out the vapor phase nitration reaction within the stated 80° C. to about 300° C. temperature range.

As is evident, the magnitude of the loss of nitrogen dioxide at temperatures higher than the usual operating temperatures and, in particular, the preferred temperature ranges, is wasteful and impractical. Moreover, if recirculation of the effluent stream from such high temperature reactions is desired, in order to prevent the complete loss of inert nitric oxide, it is necessary to employ an additional step to reoxidize the nitric oxide to reactive nitrogen dioxide by treatment thereof with oxygen or an oxygen-containing gas such as air, with the attendant added cost and complexity. The additional cost and complexity of this added step, however, is substantially reduced or eliminated altogether by the usual operating temperature conditions employed when using the nitration promoting catalysts of this invention.

Pressure is not critical in carrying out the vapor phase nitration reaction in the presence of the nitration promoting catalysts prepared in accordance with the instant process. The vapor phase nitration reaction may be carried out at subatmospheric, atmospheric, or superatmospheric pressures as desired. It will be appreciated that pressures in excess of atmospheric pressure may be advantageously employed as an aid in minimizing the previously discussed thermal decomposition of the nitrating agent, while subatmospheric pressures may be employed as an aid in vaporizing more difficult to vaporize aromatic compounds. It will be generally preferred, however, to conduct the reaction at or near atmospheric pressure. Generally, pressures from about $2.53 \times 10^4$ pascals or Pa (0.25 atmosphere or atm) to about $4.053 \times 10^5$ Pa (4.0 atm) may be conveniently employed. The term "pressure", as employed herein, when not otherwise specified, refers to gauge pressure units (Pa-G) as opposed to absolute pressure units (Pa-A).

The vapor phase nitration reaction, as previously noted, is carried out in the presence of water, which is believed necessary to create and renew reaction sites on the nitration promoting catalyst. The required water can be supplied by water of hydration in the catalyst or by the separate addition of water via the feedstream, or, alternatively, by the water present in the vaporized aqueous nitric acid when nitric acid is employed as the nitrating agent. When water of hydration (usually on the order of 5 weight percent water or less, based on the total weight of the nitration promoting catalyst) is present, or when nitric acid is employed as the nitrating agent, no separately added water is required since, in the case of catalyst water of hydration, once the reaction is initiated, water produced during the course of the reaction (1 mole of water per each 2 moles of nitroaromatic compound produced) is sufficient to sustain it. If the nitration promoting catalyst of the instant invention is substantially free of water of hydration, or if a nitrating agent other than nitric acid is employed, it then becomes necessary to add water in an amount sufficient to provide the requiring reaction sites. Separate addition of water is usually preferred to ensure its presence in sufficient amounts when a nitrating agent other than nitric acid is employed. The amount of water present, however, is not narrowly critical. Thus, amounts ranging from nominal or trace amounts (about 0.1 volume percent) up to about 15% by volume of the feedstream are generally sufficient, with amounts ranging from about 0.5% to about 5% by volume being desirably used.

As previously indicated, the vapor phase nitration reaction is conveniently carried out by continuously passing a vaporous mixture of the aromatic compound and the nitrating agent over a bed of the nitration promoting catalyst while maintaining a temperature from about 80° C. to about 300° C., and, usually, about 175° C. to about 225° C.

The reactant aromatic compound can be preheated to form a vapor which is then admixed with vaporous nitrating agent in a suitable reactor in predetermined relative proportions. The vaporous aromatic compound can be pumped into the reactor at a constant rate and admixed with vaporous nitric acid or when nitric acid is not employed as the nitrating agent, with a water-containing or humidified stream of gas and a gaseous nitrating agent, for example, nitrogen dioxide, before contacting the heated catalyst bed. Alternatively, the vaporous aromatic compound can be conveniently swept into the reactor at a constant rate by a stream of carrier gas and thence admixed with a continuous stream of nitrating agent (and water, if necessary) before contacting the heated catalyst bed. The reactants can be charged into the reactor at any suitable flow rate.

As previously indicated, the reactant materials can be conveniently swept into the reactor by a stream of carrier gas. The carrier gas employed can be oxygen or an oxygen-containing gas, or example, air, or an inert gas such as nitrogen, helium, and the like. When employed, it is advantageous to employ oxygen or an oxygen-containing gas as the carrier gas (for the aromatic compound) due to the stoichiometry of the nitration reaction between the aromatic compound and the nitrating agent, particularly, nitrogen dioxide. In addition, carrier gases preferred for separately added water and vaporous nitrating agent, respectively, are air and nitrogen, although air may be employed with nitric acid when it is the nitrating agent.

The concentration of aromatic compound in the feed mixture is not narrowly critical. All that is necessary is that the concentration be sufficient to permit the reaction to proceed at a reasonable rate. On the other hand, since the nitroaromatic compound produced will have a high vaporization temperature (for example, nitrochlorobenzene isomers, b.p., 235°–246° C.), the concentration should be such that the nitroaromatic compound produced will not condense in the reactor. In addition, since mixtures of aromatic compounds and air (the preferred aromatic compound carrier gas) are potentially flammable and explosive, it is preferred, from a practical viewpoint, to operate at concentrations outside the flammable and explosive limits of the aromatic compound being employed. Generally, concentrations between about 1% and about 15% by volume are desirably employed.

The relative proportions of reactants generally can range from about 0.5 to 5 moles of nitrating agent per mole of aromatic compound and, preferably, a ratio of about 1.0 to 4:1 is used. The preferred mole ratios, however, may vary somewhat, depending upon the choice of nitrating agent and aromatic compound employed.

The vapor phase nitration reaction is suited to either batch or continuous operations. Continuous operations can involve recirculation of the effluent stream unreacted aromatic compound and nitrating agent following isolation of the nitroaromatic compound product. Additional reactants—aromatic compounds and nitrating agent—can then be charged to the reactor along with the recirculated stream to continue the process in a subsequent and continuous reaction. It will be noted that the substantial absence of side reactions, such as, for example, the thermal decomposition of nitric acid or nitrogen dioxide and undesired by-product formation advantageously facilitates such continuous operations in that extensive purification of the effluent stream is not required.

The nitroaromatic compound produced during the course of the vapor phase nitration reaction can be collected in a suitable chilled container, and purified by any appropriate method and means known to the art such as, for example, distillation and crystallization. Fractional crystallization in accordance with conventional procedures is especially convenient for the separation of ortho and para isomers when a mono-substituted aromatic compound having an ortho-para orientation substituent, such as, chlorobenzene, is employed as the ractant or starting material.

The recovered unreacted reactants, due to the substantial absence of side-reactions to produce undesirable by-products, is easily recycled to the reactor for further processing.

The following specific examples illustrating the best presently-known methods for practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLES (a) Preparation of Group 4b-Group 3b Mixed Oxide Compositions

Example 1

Zirconium oxide ($ZrO_2$, 246.0 g, 2.00 moles) in the form of 0.32 cm×0.32 cm (0.125 inch×0.125 inch) pellets, available commercially from Harshaw Chemical Co., Cleveland, OH 44106, and 43.3 g (0.10 mole) of crystalline lanthanum nitrate hexahydrate [$La(NO_3)_3 \cdot 6H_2O$], available commercially from Fisher Scientific Co., Pittsburgh, PA 15219, were charged to a fluted, round bottom flask. The solid materials mixture was slurried with 100 ml of acetone and the flask was attached to a rotary vacuum evaporator. The acetone was removed over a 1-hour period under mild vacuum [about $8.67 \times 10^4$ Pa (650 mm Hg)] while slowly rotating the flask in a warm water bath (90°–95° C.) to leave a solid material having the shape and size of the zirconium oxide pellets. No trace of crystalline lanthanum nitrate was observed. The resulting pellets were charged to a 2.54 (1-inch) inside diameter×38.1 cm (15-inches) long stainless steel tube and calcined under nitrogen over a 2-hour period at a temperature from about 180° C. to about 200° C., the product having an empirical formula of $(ZrLa_{0.050}O_c)(NO_2)_{0.15}$.

Example 2

Titanium dioxide ($TiO_2$, 160.0 g, 2.00 moles) in the form of 0.32 cm×0.32 cm (0.125 inch×0.125 inch) pellets, available commercially from Norton Co., Akron, OH 44309, was charged to a fluted, round bottom flask equipped with an inlet tube whose lower end reached nearly to the bottom of the flask. The flask was attached to a rotary evaporator and the inlet tube was attached at the upper end to a reservoir containing 43.3 g (0.10 mole) of crystalline lanthanum nitrate hexahydrate, available commercially from Fisher Scientific Co., Pittsburgh, PA 15219, dissolved in 25 ml of water. The aqueous lanthanum nitrate solution was slowly siphoned into the flask, which was maintained under mild vacuum [about $8.67 \times 10^4$ Pa (650 mm Hg)], unto the titanium dioxide pellets over a 1-hour period while the flask was rotated in a warm water bath (90°–95° C.). The resulting pellets were calcined as described in Example 1 to yield a composition having the empirical formula ($TiLa_{0.050}O_c$)($NO_2$)$_{0.15}$.

Example 3

Titanium dioxide powder ($TiO_2$, 640.0 g, 8.00 moles), available commercially from AFTA Products, Danvers, MA 01923, was slurried with an aqueous solution of 344.0 g (0.80 mole) of lanthanum nitrate hexahydrate [$La(NO_3)_3 \cdot 6H_2O$], available commercially from Fisher Scientific Co., Pittsburgh, PA 15219, dissolved in 300 ml of water. The slurry was heated at 90° C. in an air stream to slowly evaporate the water to leave a muddy-appearing solid material. The solid material was cooled to ambient temperature and ground in a mortar to pass a 60 mesh screen (U.S. Standard Sieve Size). The powder was mixed with 1 weight percent of powdered (18 mesh, U.S. Standard Sieve Size) graphite and formed into 0.48 cm×0.48 cm (0.1875-inch×0.1875-inch) pellets. The pellets were calcined by placing them in a vacuum oven and heating at 1.33 kPa (10 mm Hg) to a temperature of 140° C., which temperature was maintained over a 2-hour period, to yield a composition having an empirical formula of ($TiLa_{0.10}O_c$)($NO_2$)$_{0.30}$.

(b) Preparation of Catalysts

Examples 4–8

A stainless steel tube, 38.1 cm (15-inches) in length and 2.54 cm (1-inch) inside diameter was employed as the reactor. A Group 4b-Group 3b mixed oxide composition was placed in the reactor to a depth of 33.02 cm (13-inches; approximately 175.0–300.0 g) and the temperature was raised to the preparation temperature, usually 180° C. When the preparation temperature was reached, sulfur dioxide, along with nitrogen dioxide (in a nitrogen carrier stream), unless specified otherwise, was charged to the reactor containing the Group 4b-Group 3b mixed oxide composition in approximately a 2-3/1 mole ratio until the sulfur trioxide uptake had reached the desired amount. The time period was usually about 2 hours. The parameters and results are tabulated in Table 1.

TABLE 1

| | | GROUP 4b–GROUP 3b MIXED OXIDE COMPOSITION[1] | | | |
|---|---|---|---|---|---|
| | | | Form | | |
| EXAMPLE | CATALYST NO. | EMPIRICAL FORMULA, $(M_a^1 M_b^2 O_c)_x (NO_2)_y$[2] | Size, cm | Shape | Amount, g[3] |
| 4 | 1 | $ZrO_2$[6] | 0.32 × 0.32 | Pellets | 283.0 |
| 5 | 2 | $(Zr_{1.0}La_{0.050}O_c)_{1.0}(NO_2)_{0.15}$ | " | " | 276.5 |
| 6 | 3 | $(Ti_{1.0}La_{0.050}O_c)_{1.0}(NO_2)_{0.15}$ | " | " | 180.0 |
| 7 | 4 | $(Ti_{1.0}La_{0.10}O_c)_{1.0}(NO_2)_{0.30}$ | 0.48 × 0.48 | " | 177.0 |
| 8 | 5 | $(Ti_{1.0}La_{0.10}O_c)_{1.0}(NO_2)_{0.30}$ | " | " | 200.0 |

| | | | CATALYST PREPARATION CONDITIONS | | | |
|---|---|---|---|---|---|---|
| | | SULFUR TRIOXIDE | Flow Rate ml/min | | | |
| | | UPTAKE | Sulfur | Nitrogen | Carrier | Time | Temp. |
| EXAMPLE | CATALYST | g, wt. %[4] | Dioxide | Dioxide | Gas[5] | Hours | °C. |
| 4 | 1 | 13.0, 4.6 | 100.0 | 50.0 | 30.0 | 2.0 | 180 |
| 5 | 2 | 12.0, 4.3 | " | " | " | " | " |
| 6 | 3 | 6.7, 3.7 | " | " | " | " | " |
| 7 | 4 | 3.6, 2.0 | " | " | " | " | " |

TABLE 1-continued

| GROUP 4b-GROUP 3b MIXED OXIDE COMPOSITION[1] | | | | | | | | |
|---|---|---|---|---|---|---|---|---|
| 8 | 5 | 2.0, 1.0 | " | " | " | " | " | |

[1]Except for zirconium oxide ($ZrO_2$) employed in Example 4 to prepare Catalyst No. 1, the Group 4b-Group 3b mixed oxide composition materials were prepared as described in Examples 1-3.
[2]Group 4b-Group 3b mixed oxide composition (catalyst precursor) material added initially to reactor.
[3]Weight in grams of Group 4b-Group 3b mixed oxide composition (catalyst precursor) material added initially to reactor.
[4]Based on the weight of the Group 4b-Group 3b mixed oxide composition material.
[5]Nitrogen; carrier gas for nitrogen dioxide.
[6]Available commercially from Harshaw Chemical Co., Cleveland, OH 44106.

(c) Use of Catalysts

Examples 9-18

Using the reactor system described in Section (a), Examples 4-8, a number of reactions were run to demonstrate the effectiveness of the nitration promoting catalysts as catalysts in the vapor phase nitration of aromatic compounds.

A stream of aromatic compound was preheated and charged to the reactor tube in a humidified or water-containing stream of air. The nitrating agent, nitrogen dioxide, in a nitrogen carrier stream was mixed with the aromatic compound/air stream shortly before contact with the heated catalyst. The products were collected in a series of three chilled containers, the first of which was chilled in an ice water bath and the second and third of which were chilled in dry ice baths. Analyses were performed by gas chromatography on a Varian Associates Model 3700 instrument using a 1.83-meter (6-ft.) by 0.32-cm (0.125-inch) outside diameter column, packed with 0.5% phosphoric acid on 5/95 weight percent SP-1000/Chromosorb G [carboxylic acid terminated poly(ethylene nitroterephthalate) from poly-(ethylene glycol), M.W., 20,000, and nitroterephthalic acid, Supelco, Inc., Bellefonte, PA 16823/diatomaceous earth, Johns-Manville Products Corp., Manville, NJ 08835] and programmed from 90° C. to 210° C. at a program rate of 10° C./min. The parameters and results are tabulated in Table 2.

TABLE 2

| | CATALYST | AROMATIC COMPOUND, R—$C_6H_5$ | | | | | |
|---|---|---|---|---|---|---|---|
| EX. | NO. | R | Flow Rate ml/min | g, mol | Conc. vol. % | Temp. °C. | Carrier Gas[3] Flow Rate ml/min |
| 9[5] | 1-P[6] | Cl | 24.6 | 40.0, 0.36 | 3.4 | 80 | 500.0 |
| 10 | 1 | " | 20.4 | 27.1, 0.24 | 3.0 | 75 | " |
| 11[5,7] | 2-P[6] | " | 22.0 | 36.0, 0.32 | 3.1 | " | " |
| 12 | 2 | " | 24.8 | 40.6, 0.36 | 3.5 | 80 | " |
| 13 | 3-P[6] | " | 26.1 | 39.1, 0.35 | 3.7 | " | " |
| 14[5,8] | 3-P[6] | " | 17.9 | 43.3, 0.37 | 2.7 | 75 | 480.0 |
| 15 | 3 | " | 21.0 | 35.1, 0.31 | 3.1 | " | 500.0 |
| 16 | 4-P[6] | " | 17.9 | 27.0, 0.24 | 2.7 | " | 480.0 |
| 17 | 4 | " | " | 27.1, 0.24 | " | " | 500.0 |
| 18 | 5[9] | " | 17.5 | 37.1, 0.33 | " | " | " |

| | NITRATING AGENT[1] | | | | | NITRATING AGENT/- |
|---|---|---|---|---|---|---|
| EX. | Flow Rate ml/min | g, mol | Conc. vol. % | Temp. °C. | Carrier Gas[4] Flow Rate ml/min | AROMATIC COMPOUND mol ratio |
| 9[5] | 41.9 | 30.3, 0.66 | 5.9 | 15 | 27.0 | 1.83 |
| 10 | 29.8 | 18.5, 0.40 | 4.6 | " | 20.0 | 1.67 |
| 11[5,7] | 51.6 | 38.1, 0.83 | 7.2 | " | 30.0 | 2.59 |
| 12 | 36.6 | 27.0, 0.58 | 5.2 | " | 25.0 | 1.61 |
| 13[5] | 35.8 | 22.1, 0.48 | 5.1 | " | 30.0 | 1.37 |
| 14[5,8] | 37.4 | 34.5, 0.75 | 5.5 | " | " | 2.03 |
| 15 | 39.4 | 26.6, 0.58 | 5.8 | " | " | 1.87 |
| 16[5] | 33.3 | 20.5, 0.45 | 4.9 | " | " | 1.88 |
| 17 | 49.1 | 24.2, 0.52 | 7.5 | " | 35.0 | 2.17 |
| 18 | 32.2 | 27.8, 0.60 | 5.2 | " | 30.0 | 1.82 |

| | WATER | | | | | REACTION CONDITIONS | |
|---|---|---|---|---|---|---|---|
| EX. | Flow Rate ml/min | g, mol | Conc. vol % | Temp. °C. | Carrier Gas[3] Flow Rate ml/min | Temp. °C. | Time hours |
| 9[5] | 15.2 | 3.8, 0.21 | 2.2 | 75 | 98.0 | 180 | 6.0 |
| 10 | 9.5 | 2.3, 0.13 | 1.4 | " | " | " | " |
| 11[5,7] | 16.0 | 4.6, 0.26 | 2.2 | " | " | " | " |
| 12 | 11.8 | 3.4, 0.19 | 1.7 | " | " | " | " |
| 13[5] | 9.0 | 1.9, 0.11 | 1.3 | " | " | " | 5.0 |
| 14[5,8] | 9.1 | 3.3, 0.18 | 1.3 | 70 | 100.0 | " | 7.5 |
| 15 | 10.9 | 2.9, 0.16 | 1.6 | 75 | 98.0 | " | 5.5 |
| 16[5] | 16.2 | 3.9, 0.22 | 2.4 | " | " | " | 6.0 |
| 17 | 10.8 | 2.1, 0.12 | 1.6 | 70 | 100.0 | " | 4.0 |
| 18 | 10.3 | 3.5, 0.19 | " | " | " | " | 7.0 |

| | | PRODUCT COMPOSITION, % | | | | | | |
|---|---|---|---|---|---|---|---|---|
| | | | R—$C_6H_4$—$NO_2$ | | | | MATERIAL BALANCE | |
| | | | R = $CH_3$, $C_2H_5O$, Cl | | | | g | |
| EX. | CONVERSION, %[2] | R = H | ortho | meta | para | para/ortho | In | Out | % |
| 9[5] | 25.0 | | 22.2 | 1.5 | 76.3 | 3.44 | 74.1 | 73.2 | 98.8 |
| 10 | 32.0 | | 22.5 | 1.8 | 75.7 | 3.36 | 47.9 | 43.8 | 91.4 |
| 11[5,7] | 10.2 | | 19.6 | 1.0 | 79.4 | 4.05 | 78.7 | 62.0 | 78.8 |

TABLE 2-continued

| | | | | | | | | |
|---|---|---|---|---|---|---|---|---|
| 12 | 64.0 | 19.3 | 1.5 | 79.2 | 4.10 | 71.0 | 70.2 | 98.9 |
| 13[5] | 17.8 | 30.9 | 2.2 | 66.9 | 2.16 | 63.1 | 65.4 | 103.6 |
| 14[5,8] | 27.5 | 27.6 | 1.5 | 70.9 | 2.56 | 79.1 | 90.5 | 114.4 |
| 15 | 80.0 | 25.2 | 1.7 | 73.1 | 2.90 | 64.6 | 64.8 | 100.3 |
| 16[5] | 37.7 | 33.4 | 2.1 | 64.5 | 1.93 | 51.4 | 47.6 | 92.6 |
| 17 | 50.0 | 24.8 | 1.8 | 73.4 | 2.96 | 53.4 | 50.0 | 93.6 |
| 18 | 46.7 | 22.3 | 1.7 | 76.0 | 3.41 | 68.4 | 65.3 | 95.4 |

[1]Nitrogen dioxide (M. W., 46) unless specified otherwise.
[2]Based on the aromatic compound.
[3]Air.
[4]Nitrogen.
[5]Comparative example to demonstrate the effectiveness of the instant invention over material without treatment for sulfur trioxide uptake.
[6]Numbered Group 4b-Group 3b mixed oxide composition (catalyst precursor) prior to treatment for sulfur trioxide uptake.
[7]Leakage at the connection to the first trap caused the loss of some material which, in turn, may have altered the conversion and product composition.
[8]The material balance was affected by water of dehydration from the catalyst.
[9]Prepared from Group 4b-Group 3b composition material prepared in accordance with the procedure described in Example 3 and having the same empirical formula as catalyst precursor 4-P.

Examples 19-20

The reactor system described for Examples 4-8 was employed. The aromatic compound and the nitrating agent, 63% nitric acid, were introduced into a vaporizer-mixer maintained at 150° C. at the approximate rates of 0.17 g (0.0015 mole) and 0.13 g (0.0013 mole) per minute, respectively, and admixed with an air carrier gas stream having a flow rate of 250.0 ml/min. The preheated mixture was then introduced into the reactor to contact the heated catalyst. The products were collected and analyzed as described for Examples 9-18. The parameters and results are tabulated in Table 3.

TABLE 3

| EX. | CATALYST NO. | AROMATIC COMPOUND, R—C6H5 | | | NITRIC ACID | | | CARRIER GAS[1] | NITRIC ACID/AROMATIC COMPOUND |
|---|---|---|---|---|---|---|---|---|---|
| | | R | g/min. | mol/min | wt % | g/min. | mol/min | ml/min | mol ratio |
| 19 | 5 | Cl | 0.55 | 0.0055 | 63.0 | 0.54 | 0.0055 | 2000.0 | 1.00 |
| 20 | " | " | 0.50 | 0.0050 | 40.0 | 0.55 | 0.0038 | 1000.0 | 0.76 |

| | REACTION CONDITIONS | | | PRODUCT COMPOSITION, % | | | | | MATERIAL BALANCE | | |
|---|---|---|---|---|---|---|---|---|---|---|---|
| | | | | | R—C6H4—NO2 | | | | | g | |
| | Temp. | Time | | | R = CH3, C2H5O, Cl | | | | | | |
| EX. | °C. | hours | CONVERSION, %[2] | R = H | ortho | meta | para | para/ortho | In | Out | % |
| 19 | 175 | 3.0 | 58.0 | | 25.0 | 1.2 | 73.8 | 2.95 | 214.0 | 195.0 | 95.0 |
| 20 | 170 | " | 65.0 | | 23.8 | 1.2 | 74.0 | 3.11 | 187.0 | 182.0 | 97.3 |

[1]Air.
[2]Based on the aromatic compound.

Thus, it is apparent that there has been provided in accordance with the instant invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for preparing a nitration promoting catalyst which comprises contacting under substantially anhydrous conditions a composition consisting essentially of a Group 4b-Group 3b mixed oxide represented by the empirical formula:

$$(M^1_a M^2_b O_c)_x (NO_2)_y$$

wherein $M^1$ is at least one element selected from Group 4b of the Periodic Table of the Elements, $M^2$ is at least one element selected from Group 3b of the Periodic Table of the Elements, a is 1, b is 0 to 20, c is a number taken to satisfy the average valences of $M^1$ and $M^2$ in the oxidation states in which they exist in the composition, x is 1, and is 0 to c, with a catalytically effective amount of sulfur trioxide.

2. The process of claim 1 wherein $M^1$ is selected from the group consisting of titanium and zirconium, and mixtures thereof, and $M^2$ is lanthanum.

3. The process of claim 2 wherein $M^1$ is titanium, $M^2$ is lanthanum, a is 1, b is 0.050 to 0.10, c is a number taken to satisfy the average valences of titanium and lanthanum in the oxidation states in which they exist in the composition, x is 1, and y is 0.15 to 0.30.

4. The process of claim 2 wherein $M^1$ is zirconium, $M^2$ is lanthanum, a is 1, b is 0.050, c is a number taken to satisfy the average valences of zirconium and lanthanum in the oxidation states in which they exist in the composition, x is 1, and y is 0.15.

5. The process of claim 1 wherein the amount of sulfur trioxide is in the range from about one weight percent to about 40 weight percent, based on the weight of the Group 4b-Group 3b mixed oxide composition.

6. The process of claim 2 wherein the contacting of the Group 4b-Group 3b mixed oxide composition with the sulfur trioxide is carried out at a temperature from about 25° C. to about 300° C.

7. The process of claim 6 wherein the temperature is from about 150° C. to about 250° C.

8. The process of claim 7 wherein the temperature is about 175° C. to about 225° C.

9. The process of claim 1 wherein the sulfur trioxide is provided by contacting the Group 4b-Group 3b oxide composition with a mixture of sulfur dioxide and nitrogen dioxide.

10. The process of claim 9 wherein the mole ratio of sulfur dioxide to nitrogen dioxide is at least 1.

11. The process of claim 10 wherein the mole ratio of sulfur dioxide to nitrogen dioxide is about 2–3/1.

12. A process for preparing a nitration promoting catalyst which comprises contacting under substantially anhydrous conditions a compositions consisting essentially of a Group 4b-Group 3b mixed oxide represented by the empirical formula:

$$(M^1{}_a M^2{}_b O_c)_x (NO_2)_y$$

wherein $M^1$ is at least one element selected from Group 4b of the Periodic Table of the Elements, $M^2$ is at least one element selected from Group 3b of the Periodic Table of the Elements, a is 1, b is 0 to 20, c is a number taken to satisfy the average valences of $M^1$ and $M^2$ in the oxidation states in which they exist in the composition, x is 1, and y is 0 to c, with a catalytically effective amount of sulfur trioxide ranging from about 3 weight percent to about 10 weight percent, based on the weight of the Group 4b-Group 3b mixed oxide composition.

* * * * *